United States Patent
Popescu et al.

[11] Patent Number: 5,867,555
[45] Date of Patent: Feb. 2, 1999

[54] ADAPTIVE DOSE MODULATION DURING CT SCANNING

[75] Inventors: Stefan Popescu, Bukarest, Romania; Dietmar Hentschel, Herzogenaurach, Germany; Karl-Ernst Strauss, Spardorf, Germany; Heiko Wolf, Tennenbronn, Germany

[73] Assignee: Siemens Aktiengesellschaft, Munich, Germany

[21] Appl. No.: 811,338

[22] Filed: Mar. 4, 1997

[51] Int. Cl.$^6$ .................................................. H61B 6/03
[52] U.S. Cl. ................................................. 378/16; 378/8
[58] Field of Search .............................. 378/8, 16, 108, 378/110, 112

[56] References Cited

U.S. PATENT DOCUMENTS

| | | | |
|---|---|---|---|
| 4,174,481 | 11/1979 | Liebetruth | 378/20 |
| 5,379,333 | 1/1995 | Toth | 378/16 |
| 5,450,462 | 9/1995 | Toth et al. | 378/16 |
| 5,485,494 | 1/1996 | Williams et al. | 378/16 |
| 5,696,807 | 12/1997 | Hsieh | 378/109 |

OTHER PUBLICATIONS

"Das 'Smart–Scan'–Verfahren der Spiral–Computeromographie: Eine neue Methode der Dosisreduktion," Giacomuzzi et al., Fortschr. Röntgenstr. 165.1 (1996) pp. 10–16, No Month.

"Dosisreduktion in der Computertomographie mit einem neuen Scan–Verfahren," Giacomuzzi et al., Akt. Radiol. vol. 6 (1996), pp. 110–113, No Month.

"Anatomisch adaptierte Variation des Röhrenstroms bei der CT," Kopka et al., Fortschr. Röntgenstr. 163.5, (1995) pp. 383–387, No Month.

*Primary Examiner*—David P. Porta
*Assistant Examiner*—David Vernon Bruce
*Attorney, Agent, or Firm*—Hill & Simpson

[57] ABSTRACT

In a method for reducing a radiation dose in an x-ray CT (computed tomography) system, a maximum x-ray attenuation per projection is computed for every projection or for every $n^{th}$ projection and the measured angular attenuation profile for a last half rotation of the x-ray beam around a subject is stored, an extrapolation method is conducted for computing an extrapolated attenuation profile for a next half rotation based on the measured angular attenuation profile for the last half rotation, and a process is conducted for setting a dose level for the x-ray beam for a next projection, based on the extrapolated attenuation profile. The x-ray beam can be modulated, with characteristics of the beam modulation being set or controlled dependent on the extrapolated attenuation profile.

7 Claims, 4 Drawing Sheets

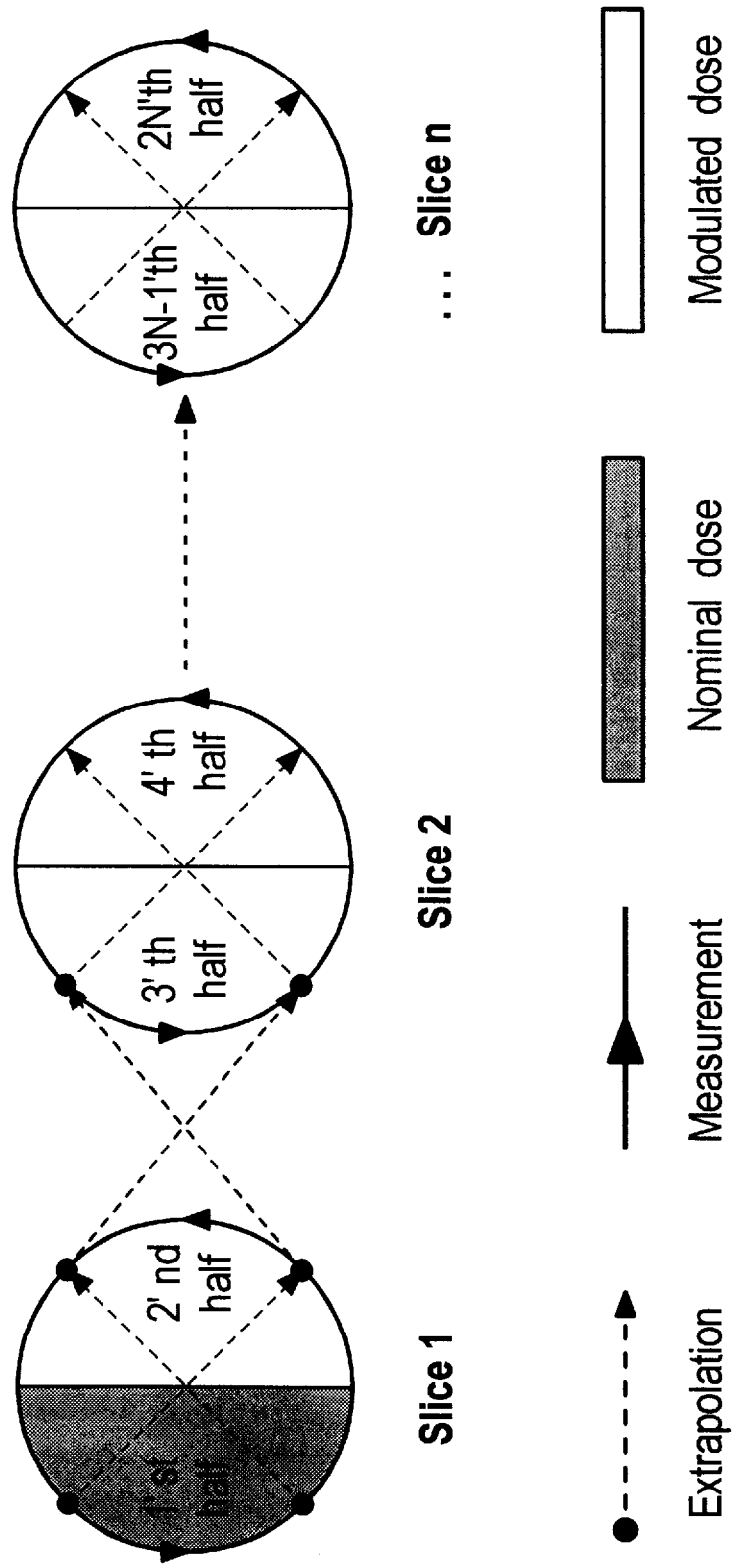

ADAPTIVE DOSE MODULATION DURING CT SCANNING

BACKGROUND OF THE INVENTION

This invention aims to reduce the dose applied to patients during computed tomography (CT) imaging and optimize the image quality by a modulation process that continuously fits the applied dose to the momentary attenuation.

The adaptive dose modulation reduces the total dose without significantly increasing noise in the final image and improves the general appearance of the image by reducing the noise streaks in anatomical regions like shoulder and pelvis.

A general computed tomography system has an x-ray source which projects a collimated, fan-shaped beam through the patient towards a bank of radiation detectors. The source and detectors are placed on a gantry that rotates around the patient. The patient table can be shifted inside the gantry, or translated. The angle and position at which the x-ray beam intersects the body can be continuously modified. Each detector produces a signal that is a measure of the body's global transparency from the source down to the detector. The set of detectors' values acquired for a particular source position is referred as a "projection". A "scan" comprises a set of projections made at different gantry or table positions. The CT system acquires many projections during 360° gantry rotation around the patient in order to build a two dimensional image or "slice" through the body. Some of the new CT systems build many slices simultaneously by using multiple rows of detectors. For every projection a "monitor" or reference detector measures the unattenuated beam intensity.

These are two systematic methods for data collection from the patient to produce CT images. The conventional "slice-by-slice" method collects the data for a complete gantry rotation with the patient in a fixed position. Between successive slices the patient is moved to a new position where the next slice can be scanned. This process continue until all planned slices have been scanned.

The "spiral" data acquisition method rotates the x-ray source around the patient while the patient couch is transported continuously through the gantry. The x-ray tube traces a spiral path with respect to the patient until the planned volume has been scanned.

For every CT acquisition mode the image quality is affected by the quantum noise, in order to keep the noise under a certain level, for every projection, the momentary x-ray power level has to be high enough so that the minimum intensity of the radiation leaving the body and reaching the detector is greater than the noise level. Most of the methods that modulate the power profile during the CT scan, used until now need two orthogonal topograms or scout views in order to acquire some information regarding the attenuation profile of the object. From the attenuation information of each topogram line a sinusoidal modulation profile is determined. However, these methods have many drawbacks:

- supplementary image noise due to a weak fit of the modulation profile to the real attenuation profile. The two orthogonal projections do not necessarily find the maximum and minimum attenuation of the slice;
- not homogeneous noise in the image due to the fact that the modulation profile does not fit to the real attenuation profile;
- patient and/or respiratory movements between topogram scan and final scan change the attenuation profile and induce extra errors.
- additionally dose used to get the scout projections;

SUMMARY OF THE INVENTION

The present invention describes a CT imaging technique in which the dose is continuously modulated based on an adaptive process. The maximum attenuation of each projection is calculated and stored. The maximum attenuation per projection as a function of gantry angle is called "angular attenuation profile". The necessary X-ray level within a half rotation is computed using an extrapolated angular attenuation profile. The extrapolation method uses the attenuation level of the previous half rotation and a priori information about the dynamic performance of the x-ray tube in order to fit the angular dose profile to the patient's angular attenuation profile.

The extrapolation method simply assumes that the angular attenuation profile of the next half rotation matches approximately the angular attenuation profile of the last half rotation. This means that the power modulation process starts only after the first half rotation of a scan, that can be a spiral scan or a slice-by-slice scan.

Another specific object of this invention is the way the attenuation is calculated during scanning with active dose modulation. The image reconstruction uses object attenuation values deduced with:

$$A_{obj} = \frac{U^{air}_{detector}}{U^{obj}_{detector}} \times \frac{U^{obj}_{monitor}}{U^{air}_{monitor}}$$

where the index air denotes measurements acquired through air (no attenuating object between x-ray tube and detectors).

Opposed to the reconstruction procedure, the dose modulation process defines a global attenuation with:

$$A_g = \frac{U^{obj}_{monitor}}{U^{obj}_{detector}}$$

This definition allows a faster calculation of the attenuation during the scan. It also avoids non-homogeneous or non-quantum noise to occur due to effects of shaped filters when using low dose to scan slices having low attenuation levels.

A more specific object of the invention is the strategy of dose modulation. The dose modulation index is limited and dependent upon the rotation time of the gantry. The angular attenuation profile is scaled to fit the allowed modulation range. The dose modulation procedure use the tube's filament temperature control in order to adjust the anode current. It is a teaching of the present invention that the modulation index is limited by the cooling time of the filament. The cooling effect produces an exponential decay of the tube current and of the radiated dose. The time constant does not depend on the nominal dose (maximal scan current). The exponential decay of the dose falling edge limits the modulation index at higher rotation speeds.

BRIEF DESCRIPTION OF THE DRAWINGS

FIG. 5 is a graphic representation of the half rotation extrapolation method.

DETAILED DESCRIPTION OF THE INVENTION

Figure 1:
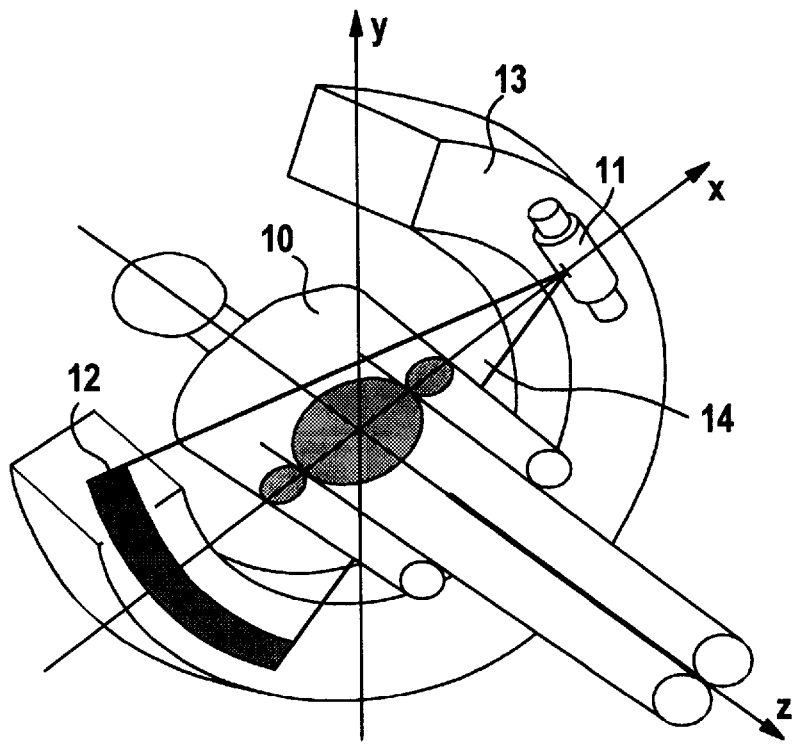
FIG. 1 CT imaging system used to build cross section images through the patient.
Figure 2A:
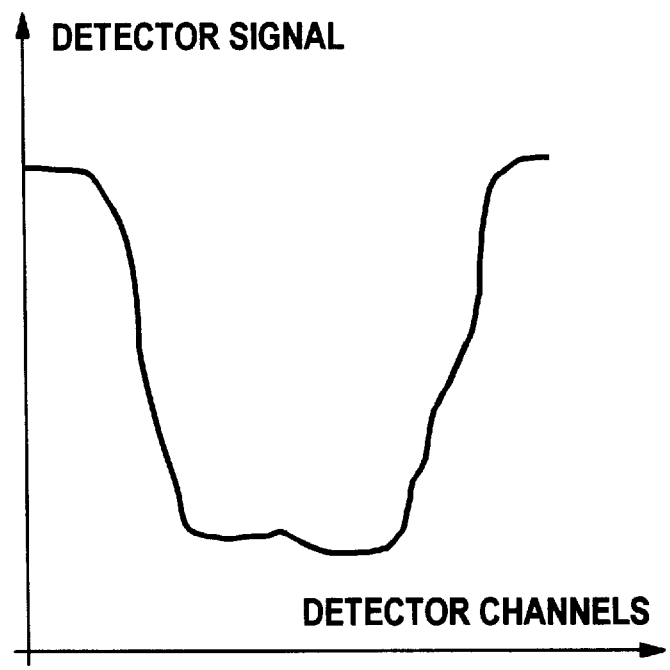
FIG. 2a is the typical signal measured at the detector bank for one projection.
Figure 2B:
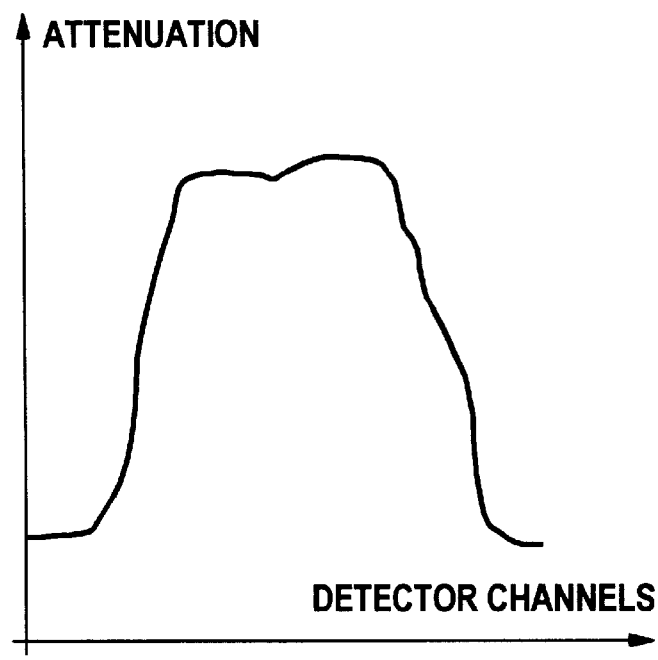
FIG. 2b is the attenuation profile for one projection.

Referring to FIG. 1 the third generation CT imaging system has an x-ray source 11 that emits a fan-shaped x-ray beam 14 toward a bank of detectors 12. Both, source and detectors, are placed on a rotationally gantry 13 able to continuously rotate around the patient. The beam cuts a slice into the patient 10 and the resulting signals at the detector channels are sampled by a data measurement system to build up a projection. FIG. 2 shows a typical signal profile for a projection. For every projection the detector that receives the lowest radiation level records the minimum signal and thus the maximum attenuation for this projection. The output of this detector is the most sensitive to quantum as well as electronic noise. In order to keep the noise under a certain level, the generator power for a projection has to be set just high enough so that the minimum level of the radiation that reaches the detectors is greater than a predefined level.

Figure 3:
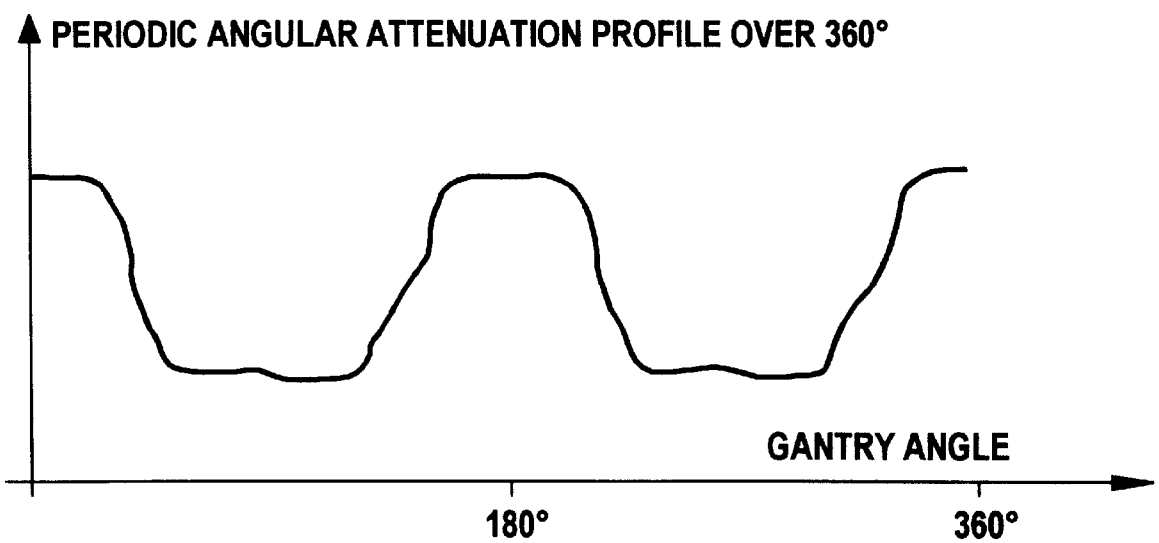
FIG. 3 is the typical angular attenuation profile for a complete revolution around the patient in the shoulder domain.

For every projection a reference detector (monitor channel) measures the unattenuated x-ray intensity, and the signal measured at this detector is used to compute the global attenuation at every other detector. The maximum attenuation per projection as a function of gantry position is the angular attenuation profile. FIG. 3 shows a typical angular attenuation profile in the shoulder domain.

Figure 4:
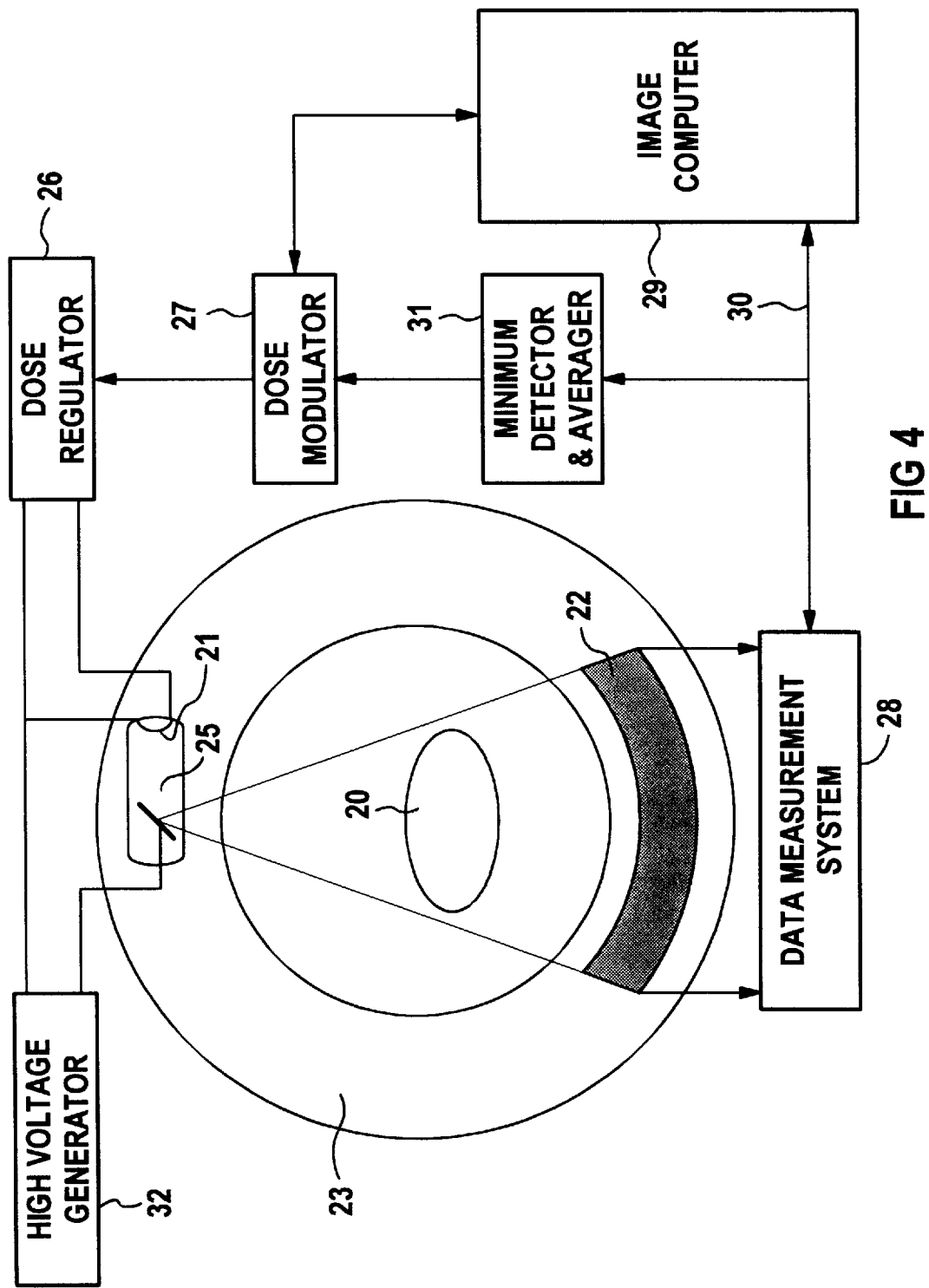
FIG. 4 is a block schematic diagram of the embodiment of the invention.

Referring to FIG. 4 the adaptive power control is a feed-back system that comprises a hardware minimum detector 31 a dose modulator 27 and the dose regulator 26. The feed-back loop closes through the x-ray source 21, the patient 20, the detector bank 22, the data measurement system 28 and the high speed data link 30 for every projection the minimum detector analysis the detector voltage and finds the minimum of the projection in the following way:

first the preprocessor module performs an offset correction for the monitor and detector values;

second a digital low pass filter implements a moving average over the projection. The period of the moving average depends on the number of detector channels;

in the case of a CT scanner with multiple rows of detectors the averaging process is bidimensional;

the dose modulator uses the monitor voltage and the minimum voltage after averaging in order to compute the maximum attenuation for the current projection:

$$A_{proj-max} = \frac{U_{monitor}}{U_{proj \cdot min}}$$

The attenuation values for a half rotation are stored for the extrapolation process. As FIG. 5 shows the extrapolation method uses the periodicity of the angular attenuation profile within a complete rotation in order to estimate the attenuation level for the next half rotation. It should be apparent that other extrapolation methods can be also used without departing from the spirit of this invention. By example the angular attenuation profile for the full rotation can be extrapolated for the next rotation.

In order to reduce the extrapolation errors, at the end of a half rotation the dose modulator performs a moving average over the measured angular attenuation profile. The period of the moving average depends on the CT machine type (time or angle projection trigger) and rotation time. The modulation index (modulation deep) for the next half rotation is given by:

$$\mu = 1 - \left(\frac{A_{min}}{A_{max}}\right)^q$$

where:

$A_{max}$=max(A$\phi$) for $\phi \in$ previous half rotation $A_{min}$=min(A$\phi$) for $\phi \in$ previous half rotation A($\phi$)=averaged angular attenuation profile of the previous half rotation $\phi$ is the gantry angle q=user supplied optimization parameter.

However, the modulation index is limited as a function of the gantry rotation speed:

if ($\mu > \mu_{max}$) then $\mu = \mu_{max}$

In a particular embodiment of the invention the following table is used for the parameter $\mu_{max}$:

| Rotation Time[s] | $\mu$max |
|---|---|
| 2.0 | 0.9 |
| 1.5 | 0.8 |
| 1.0 | 0.7 |
| 0.75 | 0.6 |

Using the extrapolated angular attenuation values the dose modulator finds the necessary dose level for the next half rotation by scaling the angular attenuation profile within the allowed modulation range with:

$$D(\phi) = D_{nominal} \cdot \left(1 - \mu \cdot \frac{A_{max}^q - A(\phi)^q}{A_{max}^q - A_{min}^q}\right)$$

where:

$D_{nominal}$ is the nominal dose (dose without modulation)

q=[0.5 ... 1] is a user supplied parameter. This parameter adjusts the efficiency of dose modulation process as follows:

q=1.—maximum dose saving q=0.5—minimum noise possible with a given dose.

The necessary dose level is obtained through the dose regulator which controls the current of the filament 21 of the x-ray tube 25.

At the beginning of the scan or whenever necessary the image computer 29 issues a sync signal that instructs the dose modulator to reinitiate the extrapolation process. The initialization period will take a half rotation. During the initialization period, the dose modulator uses the nominal dose.

We claim:

1. An adaptive method to reduce the dose by an x-ray CT system comprising the steps of:

rotating an x-ray beam around an examination subject to irradiate the subject with x-rays from a plurality of different angles in a plurality of projections;

detecting x-rays attenuated by said subject and generating detector signals corresponding thereto;

computing a maximum x-ray attenuation per projection for every projection or for every $n^{th}$ projection and storing a measured angular attenuation profile for a last half rotation;

conducting an extrapolation method for computing an extrapolated attenuation profile for a next half rotation based on the measured angular attenuation profile for the last half rotation;

conducting a process for setting a dose level for a next projection based on the extrapolated attenuation profile.

2. The method of claim 1 comprising computing the attenuation level during modulated scans using a monitor and the detector signals.

3. The method of claim 1 comprising updating and storing the angular attenuation profile every half rotation.

4. The method of claim 1 comprising reducing the extrapolation errors in the extrapolation method by applying a low pass filter over the measured angular attenuation profile.

5. The method of claim 1 comprising modulating a dose associated with said x-ray beam and controlling efficiency of the dose modulation by prescribing a user supplied optimization parameter-q.

6. The method of claim 1 wherein said x-ray beam is emitted from an x-ray tube having a tube filament, and comprising the additional steps of modulating said x-ray beam with a modulation index and limiting the modulation index as a function of speed of rotation of said x-ray beam in order to compensate for an exponential cooling time of the tube filament in pauses occurring because of the modulation.

7. The method of claim 6 comprising scaling the angular attenuation profile to fit a allowed modulation range.

* * * * *